US007074938B2

(12) United States Patent
Jacobs et al.

(10) Patent No.: US 7,074,938 B2
(45) Date of Patent: Jul. 11, 2006

(54) METHOD FOR THE SYNTHESIS OF SORITIN COMPOUNDS

(75) Inventors: Robert S. Jacobs, Santa Barbara, CA (US); R. Daniel Little, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 412 days.

(21) Appl. No.: 10/715,281

(22) Filed: Nov. 18, 2003

(65) Prior Publication Data

US 2004/0147585 A1 Jul. 29, 2004

Related U.S. Application Data

(60) Provisional application No. 60/427,245, filed on Nov. 19, 2002.

(51) Int. Cl.
*C07D 209/04* (2006.01)

(52) U.S. Cl. ...................................... 548/455; 548/452

(58) Field of Classification Search ................ 548/452, 548/455

See application file for complete search history.

(56) References Cited

U.S. PATENT DOCUMENTS

| | | | | |
|---|---|---|---|---|
| 6,291,501 | B1 * | 9/2001 | Wright et al. | 514/397 |
| 6,323,233 | B1 * | 11/2001 | Wright et al. | 514/408 |
| 6,444,697 | B1 * | 9/2002 | Wright et al. | 514/408 |
| 6,589,975 | B1 * | 7/2003 | Jacobs et al. | 514/408 |

* cited by examiner

*Primary Examiner*—Golam M. M. Shameem
(74) *Attorney, Agent, or Firm*—Suzannah K. Sundby, Esq.; Smith, Gambrell & Russell, LLP

(57) ABSTRACT

Disclosed herein are methods for synthesizing biologically active bis-heterocyclic compounds, e.g. bis-indoles. In particular, methods for making Soritin compounds such as Soritin B, bis-(1H-indol-3-yl)-acetic acid methyl ester, Soritin C, bis-2,2-(1-methyl-indol-3-yl) acetic acid methyl ester, Soritin D, bis-2,2-(1-methyl-indol-3-yl) acetic acid and Soritin compositions comprising the Soritin compounds are disclosed. Also disclosed are pharmaceutical formulations comprising the Soritin compounds and Soritin compositions.

15 Claims, 1 Drawing Sheet

METHOD FOR THE SYNTHESIS OF SORITIN COMPOUNDS

CROSS REFERENCE TO RELATED APPLICATIONS

This application claims the benefit of U.S. Provisional Patent Application No. 60/427,245, filed 19 Nov. 2002, which lists R. Daniel Little and Robert S. Jacobs as the inventors, and is herein incorporated by reference in its entirety.

BACKGROUND OF THE INVENTION

1. Field of the Invention

The present invention relates to a method for synthesizing biologically active bis-heterocyclic compounds, e.g. bis-indoles. In particular, the present invention provides methods for making Soritin compounds such as Soritin B, bis-(1H-indol-3-yl)-acetic acid methyl ester, Soritin C, bis-2,2-(1-methyl-indol-3-yl) acetic acid methyl ester, Soritin D, bis-2,2-(1-methyl-indol-3-yl) acetic acid.

2. Description of the Related Art

Bis-heterocyclic compounds, such as bis-indoles, have been previously described as having antimicrobial, antitumor or antiviral activity. See U.S. Pat. Nos. 5,955,462; 6,090,811; and 6,291,501, which are herein incorporated by reference. Specifically, the bis-indole compounds known as topsentins are disclosed in U.S. Pat. No. 4,866,084 and nortopsentins are disclosed in U.S. Pat. No. 4,970,226, which are herein incorporated by reference. Dragmacidin and its related compounds isolated from the marine sponge of the Dragmacidon sp. are disclosed in U.S. Pat. No. 4,895,844, which is herein incorporated by reference. These patents are herein incorporated by reference. These compounds as well as the homocarbonyl topsentins and hamacanthins have also been described as having inhibitory activity against cellular inflammatory responses. See U.S. Pat. Nos. 5,290,777 and 5,464,835, which are also hereby incorporated by reference.

U.S. Pat. Nos. 6,444,697 and 6,323,233 and U.S. patent application No. 20010056112 disclose bis-heterocyclic compounds known as Soritin compounds having the following formula:

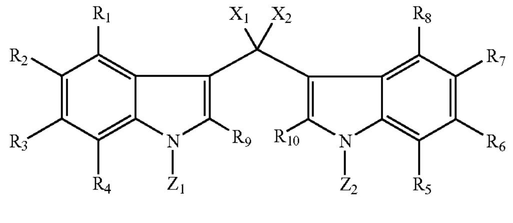

wherein $R_{1-10}$ are the same or different selected from —H, —OH, halogen, —COOH, —COOR, $C_1$–$C_8$ alkyl, $C_1$–$C_8$ alkoxyl, mesyl, tosyl, —OCOR, or $NZ_1Z_2$ (wherein the Zs can be the same or different);

$X_1$ and $X_2$ are the same or different selected from —H, —R, —COY, $C(NZ_1)Y$;

Y is —H, —OH, $NZ_1Z_2$ (wherein the $Z_1$ and $Z_2$ can be the same or different) $C_1$–$C_8$ alkyl, $C_1$–$C_8$ alkoxyl or an amino acid linked through the amine functionality forming an amide bond;

$Z_1$ and $Z_2$ are the same or different and independently selected from —H, —OH, $C_1$–$C_8$ alkyl, $C_1$–$C_8$ alkoxyl or —COR; and R is $C_1$–$C_8$ alkyl, or aryl.

The prior art patents and publications disclose methods for making a few Soritin compounds via synthetic methods that require prohibitive reaction conditions, indirect synthetic routes, and low yields. For example, Hogan and Sainsbury describe a process for making Soritin B, methyl bis(3-indolyl)-acetate which requires a temperature of −20° C. See SYNTHESIS (1984) 10:872. Likewise Amat-Guerri et al. describe a process similar to Hogan and Sainsbury which provides low yields of the desired Soritin compounds. See CHEM. LETT. (1981) 4:511–541. Earle et al. disclose a process for making Soritin C by reacting methyl chloromethoxyacetate with indole in the presence of zinc chloride at 0° C. for 8 hours. See TETRAHEDRON LETT. (1991) 32(43):6171–6174.

U.S. patent application Ser. No. 10/211,370, filed 5 Aug. 2002, discloses methods for making Soritin B and C, wherein the route of synthesis must pass through Soritin A or Soritin D. Specifically, Soritin B is made according to the following method: One-tenth (0.1) mol of indole was suspended in 500 ml of distilled water in a 1000 ml round bottom flask fitted with a reflux condenser. One-tenth (0.1) mol of glyoxylic acid (50% solution in water, Aldrich) was added to the flask. The flask was covered with foil to protect the reaction products from light. The reaction mixture was stirred and slowly heated to 50° C. using an oil bath. Once 50° C. was reached, 20 ml of 1M $H_2SO_4$ was added to the reaction mixture. The reaction mixture was heated to about 85° C. (to melt the indole) and the reaction allowed to proceed to completion (>95% conversion of indole to Soritin A). Typically, the reaction is complete within 2 hours. The reaction progress can be monitored by TLC using silica gel plates eluted with heptane-ethyl acetate 3:1 (v/v). Compounds can be visualized either by charring after treatment with 2% vanillin in $H_2SO_4$, or by UV absorbance. The product precipitates from solution as a light pink solid. The product was removed by filtration and then washed with cold distilled water to yield substantially pure Soritin A. The product was freeze-dried for 24 hours to remove water. The final yield was 0.06 mol of Soritin A.

The freeze dried Soritin A was then dissolved in 500 ml of dry methanol in a round bottom flask fitted with a reflux condenser and protected from light. Six (6) drops of concentrated $H_2SO_4$ were added to the reaction mixture which was heated to reflux for about 6 hours. The reaction progress was monitored by TLC using silica gel plates eluted with heptane-ethyl acetate 3:1 (v/v). Compounds were visualized either by charring after treatment with 2% vanillin in $H_2SO_4$, or by UV absorbance. Once the reaction was judged complete (typical conversion after 6 hours is about 60%), the solvent was reduced in volume by about two-thirds (⅔) by distillation under reduced pressure. Saturated aqueous NaCl solution (500 ml) was added. The aqueous solution was extracted three times with ethyl acetate (200 ml portions). The combined ethyl acetate extracts were then washed two times with saturated sodium bicarbonate solution (100 ml) and then dried over magnesium sulfate. The dried ethyl acetate solution was filtered to remove the $MgSO_4$, and then treated with activated carbon (100 mesh) to remove colored impurities. The filtrate was then concentrated by distillation under reduced pressure to yield the crude reaction product. To remove unreacted starting material and indole formed by decomposition of Soritin A, the material was chromatographed over silica gel using a step gradient of ethyl acetate in heptane. Fractions are monitored by TLC as above. Fractions which were substantially pure Soritin B were combined to give an isolated yield of 0.025 mol of Soritin B.

Soritin C was made according to a similar process as follows: One-tenth (0.1) mol of N-methylindole was suspended in 500 ml of distilled water in a 1000 ml round bottom flask fitted with a reflux condenser. One-tenth (0.1) mol of glyoxylic acid (50% solution in water, Aldrich) was added to the flask. The flask was covered with foil to protect the reaction products from light. The reaction mixture was stirred and slowly heated to 50° C. using an oil bath. Once 50° C. was reached, 20 ml of 1M $H_2SO_4$ was added to the reaction mixture. The reaction mixture was heated to about 80° C. and the reaction allowed to proceed to completion (>95% conversion of N-methyl indole to Soritin D). Typically the reaction is complete within 2 hours. The reaction progress can be monitored by TLC using silica gel plates eluted with heptane-ethyl acetate 3:1 (v/v). Compounds can be visualized either by charring after treatment with 2% vanillin in $H_2SO_4$, or by UV absorbance. The product precipitates from solution as a light tan solid. The product was removed by filtration and then washed with cold distilled water to yield substantially pure Soritin D. The product was freeze-dried for 24 hours to remove water. The final yield was 0.05 mol of Soritin D (VI).

The freeze dried Soritin D was then dissolved in 500 ml of dry methanol in a round bottom flask fitted with a reflux condenser and protected from light. Six (6) drops of concentrated $H_2SO_4$ were added to the reaction mixture which was heated to reflux for about 6 hours. The reaction progress was monitored by TLC using silica gel plates eluted with heptane-ethyl acetate 3:1 (v/v). Compounds were visualized either by charring after treatment with 2% vanillin in $H_2SO_4$, or by UV absorbance. Once the reaction was judged complete (typical conversion after 6 hours is about 60%), the solvent was reduced in volume by about two-thirds (⅔) by distillation under reduced pressure. Saturated aqueous NaCl solution (500 ml) was added. The aqueous solution was extracted three times with ethyl acetate (200 ml portions). The combined ethyl acetate extracts were then washed two times with saturated sodium bicarbonate solution (100 ml) and then dried over magnesium sulfate. The dried ethyl acetate solution was filtered to remove the $MgSO_4$, and then treated with activated carbon (100 mesh) to remove colored impurities. The filtrate is then concentrated by distillation under reduced pressure to yield the crude reaction product. To remove unreacted starting material, material was chromatographed over silica gel using a step gradient of ethyl acetate in heptane. Fractions were monitored by TLC as above. Fractions which were substantially pure Soritin C were combined.

Thus, the prior art methods of making Soritin compounds are indirect, i.e. have numerous process steps, and require unduly reaction conditions. Additionally, the intermediates of the prior art indirect methods breakdown, i.e. degrade, easily, thereby reducing yields and increasing degradation products or impurities. Therefore, a need still exists for faster, more efficient, easier, and higher yielding methods for making Soritin compounds and Soritin compositions having increased purity.

SUMMARY OF THE INVENTION

The present invention provides methods for making Soritin compounds having the following structural formula (A):

(A)

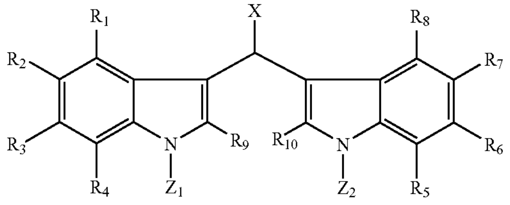

or Soritin compositions comprising the Soritin compounds, wherein $R_{1-10}$ are independently the same or different and selected from —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different);

$Z_1$ and $Z_2$ are independently the same or different and selected from —H, —OH, $C_1$–$C_8$ alkyl, cycloalkyl, $C_1$–$C_8$ alkoxyl or —COR;

R is $C_1$–$C_8$ alkyl, cycloalkyl, or aryl; and

X is —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different).

In particular, the present invention provides a method for making a Soritin compound having the following structural formula (A):

(A)

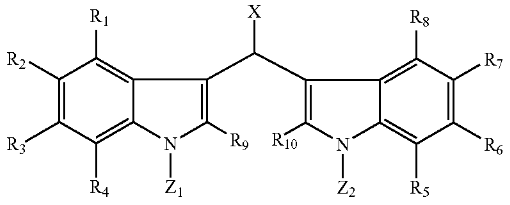

or a Soritin composition comprising the Soritin compound which comprises reacting a compound of the structural formula (I):

(1)

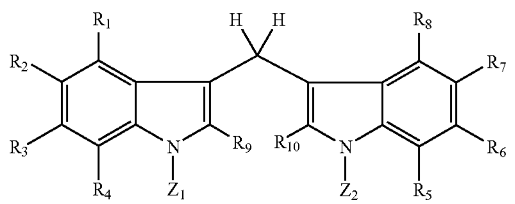

with a metallic base having the formula MB and then adding L-X, wherein L is a leaving group and X is, or is convertible to, —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different) to give the Soritin compound or the Soritin composition, wherein $R_{1-10}$ are independently the same or different and selected from —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different);

$Z_1$ and $Z_2$ are independently the same or different and selected from —H, —OH, $C_1$–$C_8$ alkyl, cycloalkyl, $C_1$–$C_8$ alkoxyl, or —COR;

R is $C_1$–$C_8$ alkyl, cycloalkyl, or aryl;

X is —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different);

M is a suitable metal ion; and

B is a suitable base.

In preferred embodiments, the leaving group is a halide, an anhydride, a mixed anhydride, or a Lewis acid complexed to S, N, or O. In some preferred embodiments, the leaving group is F, Cl, Br, I, pyridinium, substituted pyridinium, imidazolium, substituted imidazolium, $OSO_2R_{11}$, $OR_{11}$, $SR_{11}$, $OCOR_{11}$, $(R_{11})_3PO$, $OPO_3R_{11}$, or $OC({=}NR_{11})(NHR_{11})$, wherein $R_{11}$ are independently the same or different and selected from —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$. In some embodiments, the Lewis acid is coordinated to oxygen. In some embodiments, the Lewis acid includes those of boron, aluminum, zinc, copper, magnesium, and tin.

In some preferred embodiments, $Z_1$ and $Z_2$ are H or $CH_3$. In some preferred embodiments, X is —H, —$CH_3$, —COOH, or —$COOCH_3$. In some preferred embodiments, the Soritin compound is Soritin B or Soritin C. In some preferred embodiments, M is Na, K, Li, Cs, and the like. In some preferred embodiments, the base is H, $N(i\text{-}Pr)_2$, $(Si(CH_3)_3)_2$, n-BuLi, t-BuLi, sec-BuLi, $N(cyclohexyl)_2$, or N(i-Pr)(cyclohexyl). In some preferred embodiments, the metallic base is lithium diisopropylamide, sodium hydroxide, lithium hexamethyldisilazide, potassium hexamethyldisilazide, lithium tetramethylpiperidide, or potassium tetramethylpiperidide.

In some embodiments, the method further comprises concentrating the Soritin composition. In some embodiments, the method further comprises purifying the Soritin composition. In some embodiments, the Soritin composition comprises about 90% w/w or more of the Soritin compound. In some embodiments, the method yields about 90% w/w or more of the Soritin compound of the mmol of the compound having the structural formula (I) used.

In some embodiments, the present invention provides a Soritin compound or a Soritin composition made by the method of the present invention.

In some embodiments, the present invention provides a pharmaceutical or cosmetic formulation comprising the Soritin compound or the Soritin composition of the present invention and a suitable pharmaceutical or cosmetic carrier. The pharmaceutical or cosmetic formulation may further comprise at least one supplementary active compound selected from the group consisting of antibiotics, analgesics, and anti-inflammatory agents.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DETAILED DESCRIPTION OF THE INVENTION

Figure 1:
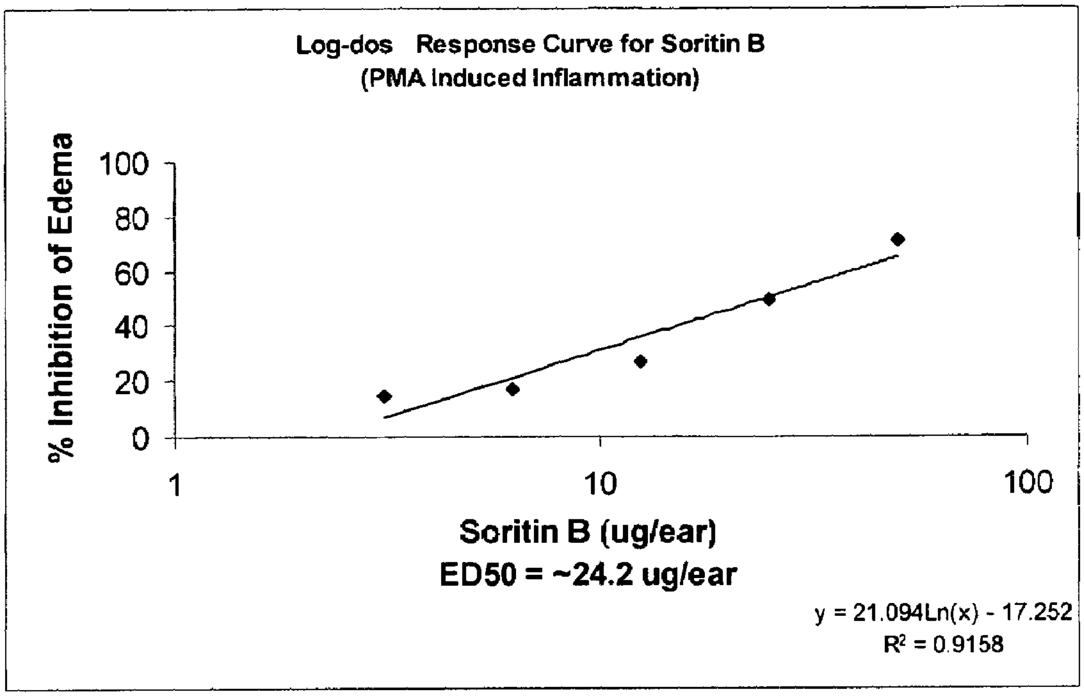
FIG. 1 shows the dose response for Soritin B as measured by percent inhibition of edema in the PMA-induced mouse ear anti-inflammatory assay.

The subject invention provides methods for making Soritin compounds having the following structural formula (A):

(A)

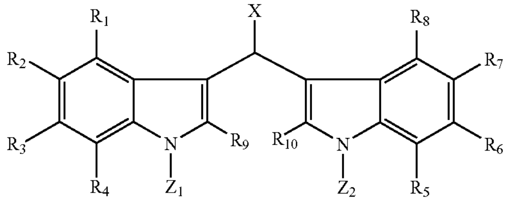

wherein $R_{1\text{-}10}$ are independently the same or different and selected from —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein the Zs can be the same or different);

$Z_1$ and $Z_2$ are independently the same or different and selected from —H, —OH, $C_1$–$C_8$ alkyl, cycloalkyl, $C_1$–$C_8$ alkoxyl, or —COR;

R is $C_1$–$C_8$ alkyl, cycloalkyl, or aryl; and

X is —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein the Zs can be the same or different).

For example, the method of the present invention may be used to make Soritin A (I), 2,2-bis(3,3'indolyl) acetaldehyde (II), Soritin B (III), Soritin C (IV), and Soritin D (V) having the following structural formulas:

(I)

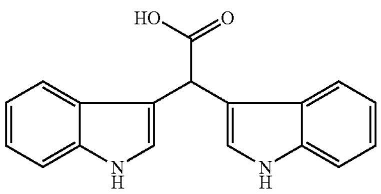

(II)

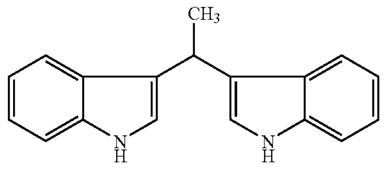

-continued (III)

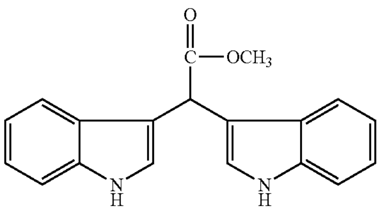

(IV)

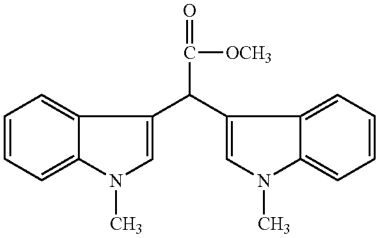

(V)

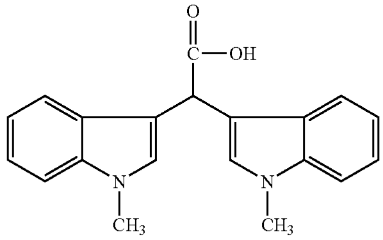

The Soritin compounds of the present invention may be made according to the following general synthetic Scheme I:

$Z_1$ and $Z_2$ are independently the same or different and selected from —H, —OH, $C_1$–Cs alkyl, cycloalkyl, $C_1$–$C_8$ alkoxyl or —COR;

R is $C_1$–$C_8$ alkyl, cycloalkyl, or aryl;

X is —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein the Zs can be the same or different;

M is a suitable metal ion such as Na, K, Li, Cs and the like;

B is a suitable base such as H; $N(i\text{-}Pr)_2$, $(Si(CH_3)_3)_2$, n-BuLi, t-BuLi, sec-BuLi, $N(cyclohexyl)_2$, and N(i-Pr)(cyclohexyl) and the like; and wherein L is a leaving group and X is, or is convertible to, —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different).

In preferred embodiments, the leaving group is a halide, an anhydride, a mixed anhydride, or a Lewis acid complexed to S, N, or O. In some preferred embodiments, the leaving group is F, Cl, Br, I, pyridinium, substituted pyridinium, imidazolium, substituted imidazolium, $OSO_2R_{11}$, $OR_{11}$, $SR_{11}$, $OCOR_{11}$, $(R_{11})_3PO$, $OPO_3R_{11}$, or $OC({=}NR_{11})(NHR_{11})$, wherein $R_{11}$ are independently the same or different and selected from —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$. In some embodiments, the Lewis acid is coordinated to oxygen. In some embodiments, the Lewis acid includes those of boron, aluminum, zinc, copper, magnesium and tin.

The starting compound (1) may be synthesized according to methods known in the art or obtained from commercial

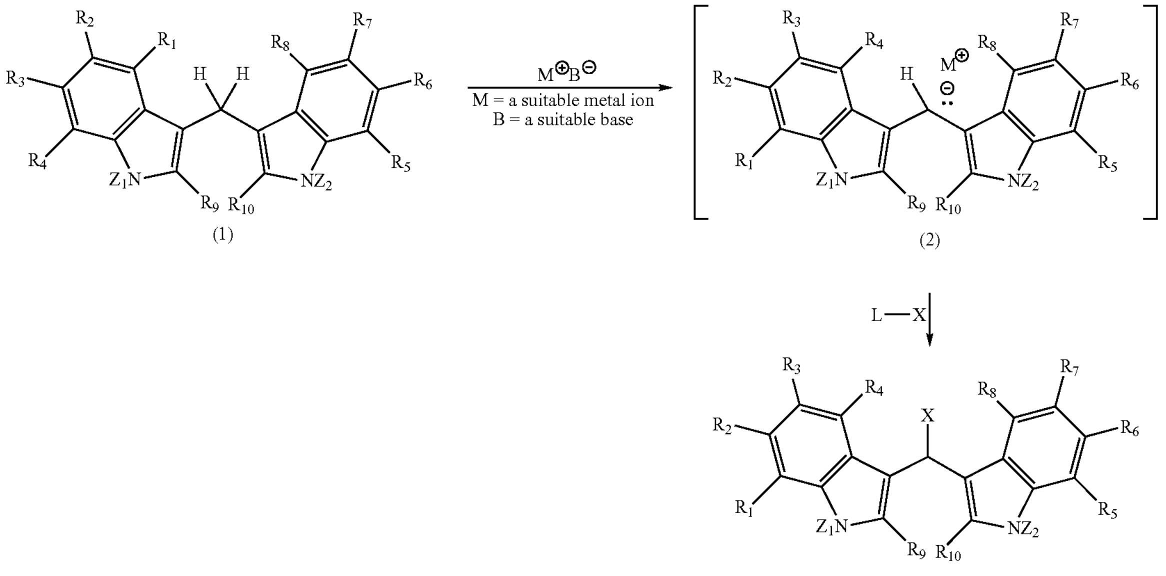

(1) (2) (A)

wherein $R_{1\text{-}10}$ are independently the same or different and selected from —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein the Zs can be the same or different);

sources. For example, 3,3'methylenebis-1H-indole may be commercially obtained from Calbiochem-Novabiochem International (San Diego, Calif.) or made by methods known in the art. Other known methyl-substituted derivatives and analogs having the general structural formula (1) may be used according to the present invention. See McDougal, A. et al. (2001) BREAST CANCER RES. TREAT. 66(2): 147–157; Kohji and Takanami (1994) Chem. Letts. 10:1915–1916; Amat-Guerri, F. et al. (1990) J. Photochem. and Photobio. 50(3):361–375; Singh and Singh (1988) Tetrahedron 44(18):5897–5904; Bergman and Eklund (1980) Tetrahedron 36(10):1439–1443; U.S. patent application Ser. No. 10/211,370, filed 5 Aug. 2002, U.S. Pat. Nos. 6,444,697 and 6,323,233 and U.S. patent application No. 20010056112, and International Patent Applications WO 0228832 and WO 9850357, which are herein incorporated by reference.

Preferred methods for making Soritin B and C are disclosed in the Examples below.

In some preferred embodiments, X is H, —$CH_3$, —COOH, or —$COOCH_3$. In some preferred embodiments, $Z_1$ and $Z_2$ are independently —H or —$CH_3$. In preferred embodiments the Soritin compound made by the method of the present invention is Soritin B, Soritin C, or Soritin D.

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

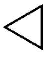, 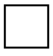, 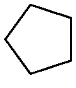, 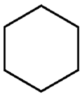, 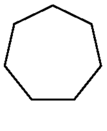,

-continued

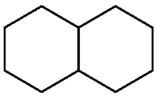, 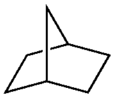, 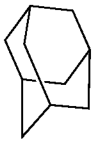,

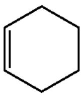, and 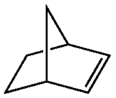.

A "heterocycloalkyl" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

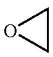, 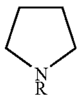, 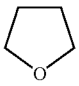, 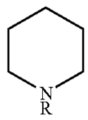, 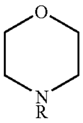, 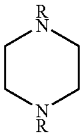,

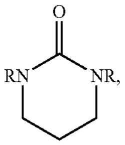, 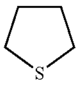, 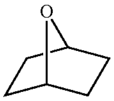, 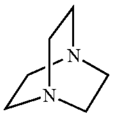,

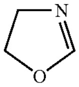, 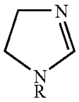, 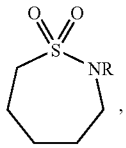, 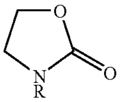,

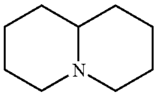, 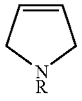, 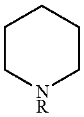, and 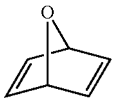.

An "aryl" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

, 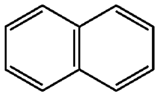, 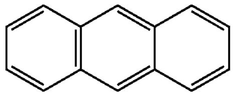, and

-continued

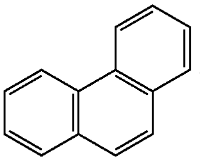.

A "heteroaryl" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

, , 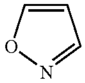, 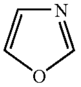, 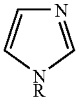, 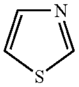,

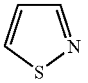, , , 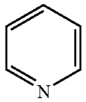, 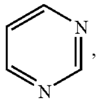,

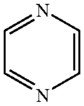, 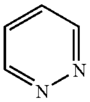, 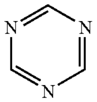, 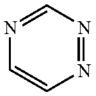, 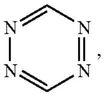,

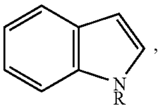, 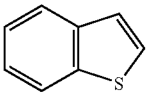, 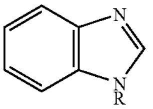,

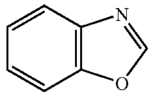, 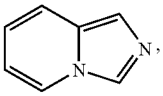, 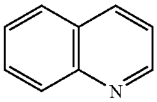,

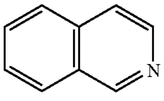, 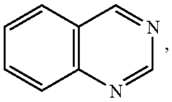, 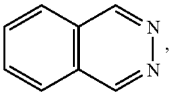,

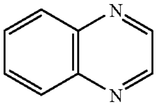, 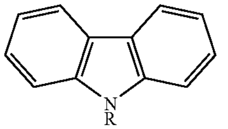,

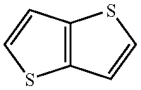, and 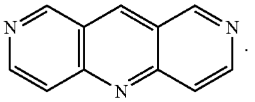.

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl" is intended to mean a —C(O)—$R^a$ radical, where $R^a$ is a suitable substituent as defined below.

A "thioacyl" is intended to mean a —C(S)—$R^a$ radical, where $R^a$ is a suitable substituent as defined below.

A "sulfonyl" is intended to mean a —$SO_2R^a$ radical, where $R^a$ is a suitable substituent as defined below.

A "hydroxyl" is intended to mean the radical —OH.

An "amino" is intended to mean the radical —$NH_2$.

An "alkylamino" is intended to mean the radical —$NHR^a$, where $R^a$ is an alkyl group.

A "dialkylamino" is intended to mean the radical —$NR^aR^b$, where $R^a$ and $R^b$ are each independently an alkyl group.

An "alkoxyl" is intended to mean the radical —$OR^a$, where $R^a$ is an alkyl group. Exemplary alkoxyl groups include methoxyl, ethoxyl, propoxyl, and the like.

An "alkoxycarbonyl" is intended to mean the radical —C(O)$OR^a$, where $R^a$ is an alkyl group.

An "alkylsulfonyl" is intended to mean the radical —$SO_2R^a$, where $R^a$ is an alkyl group.

An "alkylaminocarbonyl" is intended to mean the radical —C(O)$NHR^a$, where $R^a$ is an alkyl group.

A "dialkylaminocarbonyl" is intended to mean the radical —C(O)$NR^aR^b$, where $R^a$ and $R^b$ are each independently an alkyl group.

A "mercapto" is intended to mean the radical —SH.

An "alkylthio" is intended to mean the radical —$SR^a$, where $R^a$ is an alkyl group.

A "carboxyl" is intended to mean the radical —C(O)OH.

A "carbamoyl group" is intended to mean the radical —C(O)$NH_2$.

An "aryloxyl" is intended to mean the radical —$OR^c$, where $R^c$ is an aryl group.

A "heteroaryloxyl" is intended to mean the radical —$OR^d$, where $R^d$ is a heteroaryl group.

An "arylthio" is intended to mean the radical —$SR^c$, where $R^c$ is an aryl group.

A "heteroarylthio" is intended to mean the radical —$SR^d$, where $R^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, 3nd edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the Soritin compounds may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the Soritin compounds, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the Soritin compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See, for example, Lee et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or HSA, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011–2016; Shan, D. et al., *J. Pharm. Sci.,* 86(7):765–767; Bagshawe K., (1995) Drug Dev. Res. 34:220–230; Bodor, N., (1984) Advances in Drug Res. 13:224–331; Bundgaard, H., *Design of Prodrugs* (Elsevier Press, 1985); and Larsen, I. K., *Design and Application of Prodrugs,* Drug Design and Development (Krogsgaard-Larsen et al., eds., Harwood Academic Publishers, 1991).

If the Soritin compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the Soritin compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the Soritin compounds and salts may exist in different crystal or polymorphic forms, all of which are intended to be within the scope of the present invention and specified structural formulas.

The Soritin compounds in accordance with the present invention are useful in the treatment of inflammation and inflammatory diseases or disorders, preferably inflammation of the skin such as psoriasis and eczema. Other inflammatory diseases and disorders include osteoarthritis, rheumatoid arthritis, colitis, and Crohn's disease. The Soritin compounds may also be used in cosmetic compositions such as lotions and creams to decrease swelling and inflammation or improve the overall appearance of a subject's skin.

The anti-inflammatory activity of the Soritin compounds of the present invention may be measured by any of the methods available to those skilled in the art, including in vitro and in vivo assays. Examples of suitable assays for activity measurements are provided herein. Properties of the Soritin compounds may be assessed, for example, by using one or more of the assays set out in the Examples below. Other pharmacological methods may also be used to determine the efficacy of the compounds as anti-inflammatory compounds.

For purposes of the subject invention, unless otherwise noted, the terms "inflammation" and "inflammatory response" refer to any and all such inflammatory reactions including, but not limited to, immune-related responses and/or allergic reactions to a physical, chemical, or biological stimulus. "Anti-neurogenic inflammatory activity," as used herein, will be understood by those of ordinary skill in the art to mean biological activity inhibiting or controlling a neurogenic inflammatory response.

The compounds of the subject invention can be used to treat a variety of skin conditions including, but not limited to, radiation irritation and burns (including UV and ionizing), chemical burns, rhinitis, thermal burns, and reddening of the skin, as well as neurogenic inflammation, present in different processes, such as diabetes, asthma, cystitis, gingivitis, migraine, dermatitis, psoriasis, inflammation of sciatic and lumbar nerves, gastrointestinal processes, ocular inflammation, and acute allergic response, poison oak, rheumatoid arthritis, osteoarthritis and other inflammatory conditions involving acute and/or chronic joint inflammation in a subject, preferably mammalian, more preferably human. The compounds of the subject invention can also be used to promote wound healing and prevent or inhibit pain.

The Soritin compounds of the present invention may be used in combination with or as a substitution for treatments of the above conditions. For example, the Soritin compounds may also be used alone or combination with an anti-neoplastic agent to treat cancer. The Soritin compounds of the invention may be used alone or in combination with glucocorticoids, cyclooxygenase (COX) inhibitors, aspirin, or methotrexate to treat inflammatory disorders such as rheumatoid arthritis. Further, the Soritin compounds of the present invention may be used alone or in combination with analgesics to treat, prevent or inhibit pain.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

A Soritin compound of the present invention may be administered in a therapeutically effective amount to a mammal such as a human. Therapeutically effective amounts of the Soritin compounds of the invention may be used to treat, modulate, attenuate, reverse, or affect the inflammatory pathway in a mammal. The inflammatory pathway may be either the immunogenic inflammatory pathway, the neurogenic inflammatory pathway, or both. An "effective amount" is intended to mean that amount of an agent that, is sufficient to treat, prevent, or inhibit cytokine or eicosanoid production or neutrophil influx. Thus, e.g., a "therapeutically effective amount" of a Soritin compound, a prodrug, an active metabolite, or a salt thereof, is a quantity sufficient to, when administered to a mammal, treat, prevent, or inhibit cytokine or eicosanoid production or neutrophil influx in the mammal. The amount of a given Soritin that will correspond to such an amount will vary depending upon factors such as the given drug or compound, the pharmaceutical formulation and route of administration, the type of inflammatory disease or disorder, the type of inflammation, and the identity of the subject or host being treated, but can nevertheless be routinely determined by one skilled in the art. Also, as used herein, a "therapeutically effective amount" of an Soritin compound of the present invention is an amount which prevents, inhibits, suppresses, or reduces the amount of inflammation as caused by an irritant, such as PMA, in a subject as compared to a control. As defined herein, a therapeutically effective amount of a compound of the present invention may be readily determined by one of ordinary skill by routine methods known in the art.

For example, a therapeutically effective amount of a compound of the invention ranges from about 0.1 to about 1,000 mg/kg body weight, preferably about 0.1 to about 500 mg/kg body weight, and more preferably about 0.1 to about 100 mg/kg body weight. The skilled artisan will appreciate that certain factors may influence the dosage required to effectively treat a subject, including but not limited to the severity of the disease or disorder, previous treatments, the general health and/or age of the subject, and other diseases present.

Preferred topical concentrations include about 0.1% to about 10% of at least one Soritin compound in a formulated salve. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the Soritin compound may consist of a single administration, or alternatively comprise a series of applications. For example, a subject may be treated with a Soritin compound of the invention at least once. However, the subject may treated with the Soritin compound from about one time per week to about once daily for a given treatment period. The length of the treatment period will depend on a variety of factors such as the severity of inflammation, the concentration and activity of the Soritin composition, or a combination thereof. It will also be appreciated that the effective dosage of the compound used for treatment may increase or decrease over the course of a particular treatment. Changes in dosage may result and become apparent by standard diagnostic assays known in the art. In some instances chronic administration may be required. The Soritin compound may be administered before, during, after, or a combination thereof exposure to an irritant that causes inflammation.

As the method of the present invention will provide a Soritin composition having a yield, of about 90% or more, that is greater than the prior art methods, the Soritin composition resulting from the method may be directly incorporated into pharmaceutical formulations. Thus, the present invention provides pharmaceutical formulations comprising more potent Soritin compositions, which comprise higher concentrations of at least one Soritin compound.

The pharmaceutical formulations of the invention comprising higher yielding Soritin compositions may be prepared in a unit-dosage form appropriate for the desired mode of administration. The pharmaceutical formulations of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen Soritin compound.

It will be appreciated that the actual dosages of the compounds used in the pharmaceutical formulations of this invention will vary according to the particular complex being used, the particular composition formulated, the mode of administration, and the particular site, host, and disease being treated. Optimal dosages for a given set of conditions may be ascertained by those skilled in the art using conventional dosage determination tests in view of the experimental data for a given Soritin compound. Administration of prodrugs may be dosed at weight levels that are chemically equivalent to the weight levels of the fully active forms.

The Soritin compounds or Soritin compositions of the invention can be incorporated into pharmaceutical formulations suitable for administration. Pharmaceutical formulations of this invention comprise a therapeutically effective amount of at least one Soritin compound, and an inert, pharmaceutically or cosmetically acceptable carrier or diluent. As used herein the language "pharmaceutically or cosmetically acceptable carrier" is intended to include any and all solvents, dispersion media, coatings, antibacterial and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically or cosmetically active substances is well known in the art.

Except insofar as any conventional media or agent is incompatible with the active compound, use thereof in the formulation is contemplated. Supplementary active compounds can also be incorporated into the formulations. Supplementary active compounds include anti-inflammatory agents and analgesics and other compounds commonly used to treat inflammation or commonly used in cosmetics to enhance the skin of a subject such as color and elasticity.

A pharmaceutical or cosmetic formulation of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0–60% of the total volume. In an exemplary embodiment, the Soritin compound of the present invention is dissolved in DMSO and diluted with water.

The pharmaceutical formulation may also be in the form of a solution of a salt form of the active ingredient in an appropriate aqueous vehicle such as water or isotonic saline or dextrose solution.

The pharmaceutical formulations of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical formulations may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the Soritin compounds and Soritin compositions can be formulated readily by combining with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (compound), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds and agents.

Pharmaceutical formulations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the formulations may take the form of tablets or lozenges formulated in conventional manner.

Oral formulations generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral formulations can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the Soritin compounds or Soritin compositions of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The Soritin compounds or Soritin compositions of the present invention may be formulated for parenteral administration by injection, e.g., by bolus injection or continuous infusion. Formulations for injection may be presented in unit-dosage form, e.g., in ampoules or in multi-dose containers, with an added preservative. The formulations may take such forms as suspensions, solutions or emulsions in oily or aqueous vehicles, and may comprise formulatory agents such as suspending, stabilizing and/or dispersing agents.

Pharmaceutical formulations suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the formulation. Prolonged absorption of the injectable compositions can be brought about by including in the formulation an agent which delays absorption, for example, aluminum monostearate and gelatin.

Sterile injectable solutions can be prepared by incorporating a therapeutically effective amount of a Soritin compound or Soritin composition of the present invention in an appropriate solvent with one or a combination of ingredients enumerated above, as required, followed by filtered sterilization. Generally, dispersions are prepared by incorporating the Soritin compound or Soritin composition of the present invention into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients or cosmetically acceptable carriers and additives include solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the Soritin compound or Soritin composition of the present invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. Soritin compounds or Soritin compositions of the present invention may also be injected directly into the vitreous and aqueous humor.

Alternatively, Soritin compounds or Soritin compositions of the present invention may be in powder form for constitution with a suitable vehicle, e.g., sterile pyrogen-free water, before use. The Soritin compounds or Soritin compositions of the present invention may also be formulated in rectal compositions such as suppositories or retention enemas, e.g., comprising conventional suppository bases such as cocoa butter or other glycerides.

In addition to the formulations described above, the Soritin compounds or Soritin compositions of the present invention may also be formulated as a depot preparation. Such long-acting formulations may be administered by implantation (for example, subcutaneously or intramuscularly) or by intramuscular injection. Thus, for example, the Soritin compounds or Soritin compositions of the present invention may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical formulations may be employed. Liposomes and emulsions are known examples of delivery vehicles or carriers for hydrophobic drugs and cosmetics. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical formulations also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, and the like. Salts tend to be more soluble in aqueous or other protonic solvents than are the corresponding free-base forms.

In one embodiment, the Soritin compounds or Soritin compositions of the present invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

It is especially advantageous to formulate oral or parenteral formulations in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The following examples are intended to illustrate but not to limit the invention.

EXAMPLE 1

Synthesis of Soritin B

Soritin B may be made according to the following method: About one equivalent of 0.5 M solution of 3,3'-methylenebis-1H-indole dissolved in THF is treated with about 3.0 equivalents of a suitable metallic base MB, wherein M=Na, K, Li, Cs, and the like and B=H, $N(i\text{-}Pr)_2$, $(Si(CH_3)_3)_2$, n-BuLi, t-BuLi, sec-BuLi, $N(cyclohexyl)_2$, and N(i-Pr)(cyclohexyl) and the like, at or below room temperature. The solution is stirred for about 0.5 to about 1 hour and then about 0.1 M solution of about 1.0 equivalent of methyl chloroformate in THF is added dropwise with stirring. The time course for the reaction may be monitored by the disappearance of the starting material by TLC (silica gel, 2:1 (v/v) petroleum ether/ethyl acetate). When the reaction is finished, the reaction mixture is diluted with brine and extracted about 3 to about 4 times with ethyl acetate. The combined extracts are washed with saturated aqueous sodium bicarbonate, dried over anhydrous magnesium sulfate, filtered, and concentrated in vacuo to give Soritin B as a tan powder in about a 90% yield or more.

EXAMPLE 2

Synthesis of Soritin C

Soritin C may be made according to the following method: About one equivalent of 0.5 M solution of 3.3'-methylenebis(1-methyl-1H-indole) dissolved in THF is treated with about 1.05 equivalents of a suitable metallic base MB, wherein M=Na, K, Li, Cs, and the like and B=H, N(i-Pr)$_2$, (Si(CH$_3$)$_3$)$_2$, n-BuLi, t-BuLi, sec-BuLi, N(cyclohexyl)$_2$, N(i-Pr)(cyclohexyl), tetramethylpiperidide and the like, at or below room temperature. The solution is stirred for about 0.5 to about 1 hour and then about 0.1 M solution of about 1.0 equivalent of methyl chloroformate in THF is added dropwise with stirring. The time course for the reaction may be monitored by the disappearance of the starting material by TLC (silica gel, 2:1 (v/v) petroleum ether/ethyl acetate). When the reaction is finished, the reaction mixture is diluted with brine and extracted about 3 to about 4 times with ethyl acetate. The combined extracts are washed with saturated aqueous sodium bicarbonate, dried over anhydrous magnesium sulfate, filtered, and concentrated in vacuo to give Soritin C as a tan powder in about a 90% yield or more.

EXAMPLE 3

Inhibition of PMA-Induced Inflammation (Edema) of the Mouse Ear

The test compound made by the method of the present invention and a known inflammatory agent, phorbol myristate acetate (PMA), are topically applied simultaneously to the left ears of mice. Three hours and 20 minutes following application, the mice are sacrificed. Both left ears and right ears are removed and standard sized bores taken. Edema (inflammation) is measured as the difference in weight between left and right ears. See Van Arman, C. G. (1974) *Clin. Pharmacol. Ther.* 16:900–904, which is herein incorporated by reference.

EXAMPLE 4

Inhibition of Resiniferatoxin-Induced Inflammation (Edema) of the Mouse Ear

Induction of mouse ear edema can be conducted according to known methods. See Inoue, 1-f., N. Nagata, Y. Koshffiara (1993), which is herein incorporated by reference. Soritin compounds to be tested for anti-neurogenic inflammatory activity are topically applied in acetone to the ears of mice in a solution that includes the edema-causing irritant resiniferatoxin (RTX). RTX alone (0.1 μg/ear) or in combination with various dilutions of test compound are applied to both sides of the left ears (5 mice per treatment group) and acetone is applied to all right ears. After a 30-minute incubation, the mice are sacrificed, the ears removed, and bores taken and weighed. Edema is measured by subtracting the weight of the right ear (acetone control) from the weight of the left ear (treated). Results are recorded as % decrease (inhibition) or % increase (potentiation) in edema relative to the control group edema.

EXAMPLE 5

Soritin B Assay

The following assay was conducted to determine whether Soritin B had coloration in solution and when applied to skin and whether Soritin B exhibited anti-inflammatory properties.

Soritin B was dissolved in acetone and exhibited a light amber color. Soritin B in acetone alone and in combination with phorbol myristate acetate or resiniferatoxin did not exhibit any discernable coloration on test ears from the beginning to the end of the experiments provided herein. Thus, there was no coloration due to application of Soritin B. Additionally, overnight exposure to Soritin B did not result in any discernable redness or swelling at 50 μg/ear when compared to controls.

A. Inhibition of PMA-Induced Inflammation (Edema) of the Mouse Ear

Soritin B and a known inflammatory agent, phorbol myristate acetate (PMA), were topically applied simultaneously to the left ears of mice. Three hours and 20 minutes following application, the mice were sacrificed. Both left ears and right ears were removed and standard sized bores taken. Edema (inflammation) was measured as the difference in weight between left and right ears. See Van Arman, C. G. (1974) *Clin. Pharmacol. Ther.* 16:900–904, which is herein incorporated by reference.

Soritin B proved to be capable of reducing edema in mouse ears caused by application of phorbol myristate acetate (PMA). At a dose of 50 μg/ear of Soritin B, PMA-induced edema was inhibited by about 71.3%. The $ED_{50}$ for inhibition of PMA-induced edema was observed to be 24.2 μg/ear. See Table 1 and FIG. 1.

TABLE 1

| Treatment | Mean | SEM | % Inh. Of Edema |
|---|---|---|---|
| PMA Control 2.0 μg/ear n = 15 | 11.8 | 0.6 | |
| Soritin B 50 μg/ear n = 15 | 3.4* | 0.5 | 71.3 |
| Soritin B 25 μg/ear n = 15 | 5.9* | 0.7 | 50.0 |
| Soritin B 12.5 μg/ear n = 15 | 8.6* | 0.7 | 27.1 |
| Soritin B 6.25 μg/ear n = 15 | 9.7** | 0.5 | 17.1 |
| Soritin B 3.12 μg/ear n = 15 | 10.0** | 0.4 | 14.6 |

*Statistically significant difference between control and experimental group (T-test, $p < 0.01$)
**Statistically significant difference between control and experimental group (T-test, $p < 0.05$)

B. Inhibition of Resiniferatoxin-Induced Inflammation (Edema) of the Mouse Ear

Soritin B was tested for anti-neurogenic inflammatory activity by topically applying in acetone to the ears of mice in a solution that includes the edema-causing irritant resiniferatoxin (RTX) as provided above. See Inoue, 1-f., N. Nagata, Y. Koshffiara (1993), which is herein incorporated by reference. Specifically, RTX alone (0.1 μg/ear) or in combination with various dilutions of Soritin B was applied to both sides of the left ears (5 mice per treatment group) and acetone was applied to all right ears. After a 30-minute incubation, the mice are sacrificed, the ears removed, and bores taken and weighed. Edema was measured by subtracting the weight of the right ear (acetone control) from the weight of the left ear (treated). Results were recorded as % decrease (inhibition) or % increase (potentiation) in edema relative to the control group edema.

Figure 2:
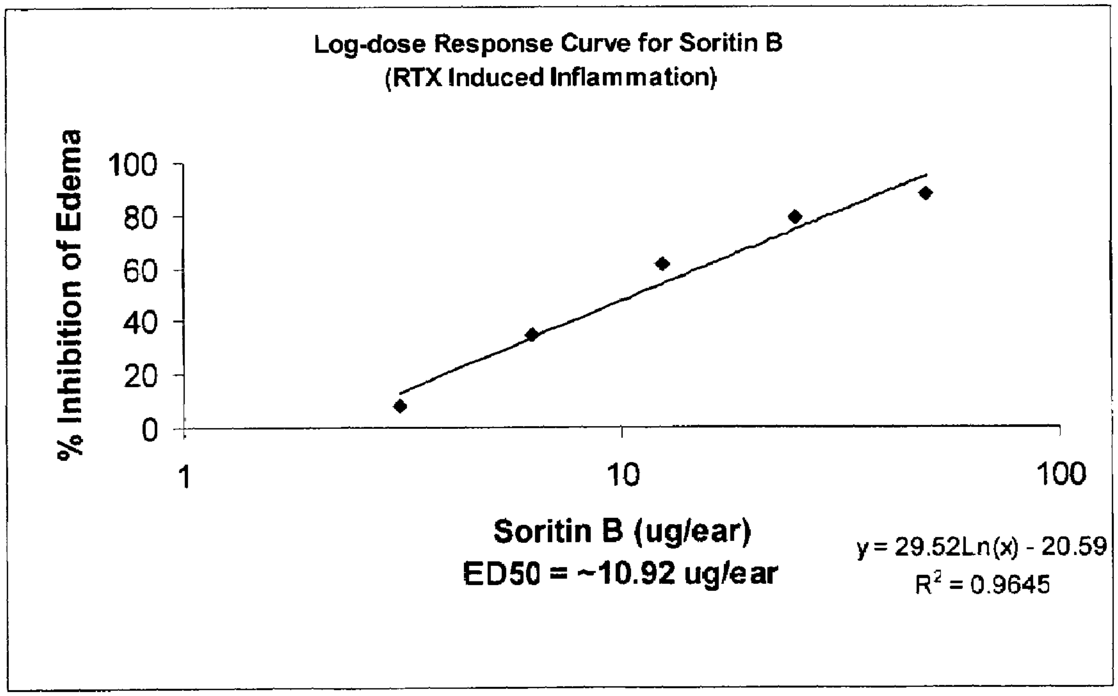
FIG. 2 shows the dose response for Soritin B as measured by percent inhibition of edema in the RTX-induced mouse ear anti-inflammatory assay.

Soritin B proved to be capable of reducing edema in mouse ears caused by application of resiniferatoxin (RTX). At a dose of 50 μg/ear of Soritin B, RTX-induced edema was inhibited by about 87.6%. The $ED_{50}$ for inhibition of RTX-induced edema was observed to be 10.9 μg/ear. See Table 2 and FIG. 2.

TABLE 2

| Treatment | Mean | SEM | % Inh. Of Edema |
|---|---|---|---|
| RTX Control 0.1 μg/ear n = 15 | 8.3 | 0.4 | |
| Soritin B 50 μg/ear n = 15 | 1.0* | 0.2 | 87.6 |
| Soritin B 25 μg/ear n = 14 | 1.7* | 0.3 | 79.2 |
| Soritin B 12.5 μg/ear n = 15 | 3.2* | 0.4 | 61.0 |
| Soritin B 6.25 μg/ear n = 15 | 6.5* | 0.5 | 34.3 |
| Soritin B 3.12 μg/ear n = 15 | 9.1 | 1.0 | 7.7 |

*Statistically significant difference between control and experimental group (t-test, $p < 0.01$)

To the extent necessary to understand or complete the disclosure of the present invention, all publications, patents, and patent applications mentioned herein are expressly incorporated by reference therein to the same extent as though each were individually so incorporated.

It should be understood that the examples and embodiments described herein are of illustrative purposes only and that various modification or changes in light thereof will be suggested to persons skilled in the art and are to be included within the spirit and purview of this application and the scope of the appended claims.

What is claimed is:

1. A method for making a Soritin compound or having the following structural formula (A):

(A)

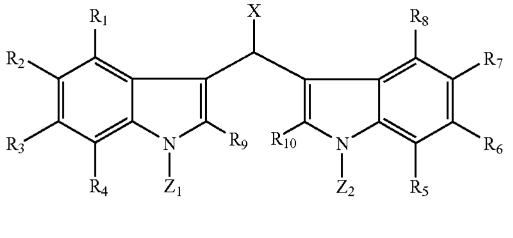

or a Soritin composition comprising the Soritin compound which comprises reacting a compound of the structural formula (1):

(1)

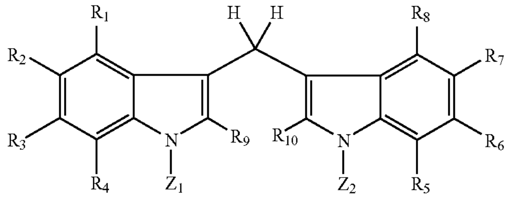

with a metallic base having the formula MB and then adding L-X, wherein L is a leaving group and X is, or is convertible to, —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different) to give the Soritin compound or the Soritin composition, wherein $R_{1-10}$ are independently the same or different and selected from —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different);

$Z_1$ and $Z_2$ are independently the same or different and selected from —H, —OH, $C_1$–$C_8$ alkyl, cycloalkyl, $C_1$–$C_8$ alkoxyl, or —COR;

R is $C_1$–$C_8$ alkyl, cycloalkyl, or aryl;

X is —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$ (wherein $Z_1$ and $Z_2$ can be the same or different);

M is a suitable metal ion; and

B is a suitable base.

2. The method of claim 1, wherein $Z_1$ and $Z_2$ are H or $CH_3$.

3. The method of claim 1, wherein X is —H, —$CH_3$, —COOH, or —$COOCH_3$.

4. The method of claim 1, wherein the Soritin compound is Soritin B.

5. The method of claim 1, wherein the Soritin compound is Soritin C.

6. The method of claim 1, wherein M is Na, K, or Li.

7. The method of claim 1, wherein M is Na, K, Li, or Cs, and B is H, $N(i\text{-}Pr)_2$, $(Si(CH_3)_3)_2$, n-BuLi, t-BuLi, sec-BuLi, $N(cyclohexyl)_2$, N(i-Pr)(cyclohexyl), tetramethylpiperidide.

8. The method of claim 1, wherein the metallic base is lithium diisopropylamide, sodium hydroxide, lithium hexamethyldisilazide, potassium hexamethyldisilazide, lithium tetramethylpiperidide, or potassium tetramethylpiperidide.

9. The method of claim 1, wherein the leaving group is a halide, an anhydride, a mixed anhydride, or a Lewis acid complexed to S, N, or O.

10. The method of claim 1, wherein the leaving group is F, Cl, Br, I, pyridinium, substituted pyridinium, imidazolium, substituted imidazolium, $OSO_2R_{11}$, $OR_{11}$, $SR_{11}$, $OCOR_{11}$, $(R_{11})_3PO$, $OPO_3R_{11}$, or $OC(=NR_{11})(NHR_{11})$, wherein $R_{11}$ are independently the same or different and selected from —H, —OH, halogen, —COOH, —COOR, $C_1$–$C_8$ alkyl, cycloalkyl, $C_1$–$C_8$ alkoxyl, mesyl, tosyl, mesyloxy, tosyloxy, arylsulfonyl, arylsulfonyloxy, —OCOR, or $NZ_1Z_2$.

11. The method of claim 9, wherein the Lewis acid is coordinated to oxygen.

12. The method of claim 9, wherein the Lewis acid includes boron, aluminum, zinc, copper, and tin.

13. The method of claim 1, wherein the Soritin composition is further concentrated.

14. The method of claim 1, wherein the Soritin composition is purified.

15. The method of claim 1, wherein the Soritin composition comprises about 90% w/w or more of the Soritin compound.

* * * * *